United States Patent
Arnold et al.

(10) Patent No.: US 8,886,270 B2
(45) Date of Patent: Nov. 11, 2014

(54) SYRINGE-BASED WHISPERING GALLERY MODE MICRORESONATOR MICROFLUIDIC BIOCHEM SENSOR

(75) Inventors: Stephen Arnold, New York, NY (US); Siyka Shopova, Staten Island, NY (US); Ying Chen, Brooklyn, NY (US); William Chin, Rego Park, NY (US); Guyu Liu, Brooklyn, NY (US); Raaj Haresh Rajmangal, South Ozone Park, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 849 days.

(21) Appl. No.: 13/090,836

(22) Filed: Apr. 20, 2011

(65) Prior Publication Data

US 2011/0306854 A1    Dec. 15, 2011

Related U.S. Application Data

(60) Provisional application No. 61/326,098, filed on Apr. 20, 2010.

(51) Int. Cl.
| | |
|---|---|
| *A61B 5/1455* | (2006.01) |
| *G02B 6/26* | (2006.01) |
| *A61M 5/178* | (2006.01) |
| *G02B 6/293* | (2006.01) |
| *G01N 33/543* | (2006.01) |
| *A61B 5/1473* | (2006.01) |
| *A61B 5/1459* | (2006.01) |
| *A61B 5/00* | (2006.01) |
| *G01N 21/77* | (2006.01) |

(52) U.S. Cl.
CPC ........ *G01N 21/77* (2013.01); *G01N 2021/7789* (2013.01); *A61M 5/178* (2013.01); *G02B 6/29356* (2013.01); *G02B 6/29341* (2013.01); *G01N 33/54366* (2013.01); *A61B 5/1473* (2013.01); *A61B 5/1459* (2013.01); *A61B 5/6848* (2013.01)
USPC .............................. 600/341; 600/342; 385/32

(58) Field of Classification Search
USPC ............... 600/310, 322, 341, 342; 385/28, 32
See application file for complete search history.

(56) References Cited

U.S. PATENT DOCUMENTS

| | | | | |
|---|---|---|---|---|
| 4,622,974 | A * | 11/1986 | Coleman et al. | 600/342 |
| 6,490,039 | B2 * | 12/2002 | Maleki et al. | 385/30 |
| 7,693,369 | B2 * | 4/2010 | Fan et al. | 385/32 |

* cited by examiner

*Primary Examiner* — Eric Winakur
(74) *Attorney, Agent, or Firm* — John C. Pokotylo; Straub & Pokotylo

(57) ABSTRACT

A syringe-based whispering gallery mode sensor includes a syringe including an assembly provided its needle, the assembly including (1) an optical carrier having a reflective distal end, and (2) at least one resonator coupled with the optical carrier. This sensor may be provided in a system including a light source, a light detector, and a data analysis component. A method for determining the presence or concentration of a target substance in body fluid may be performed using such a system.

20 Claims, 15 Drawing Sheets

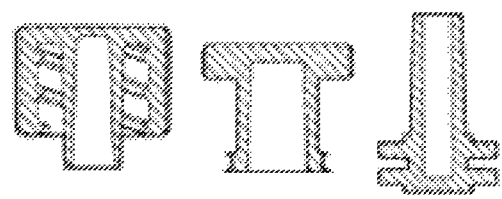
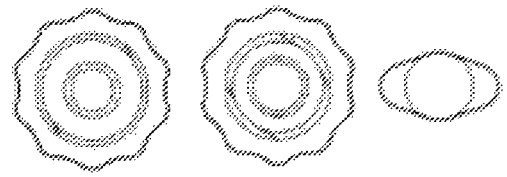
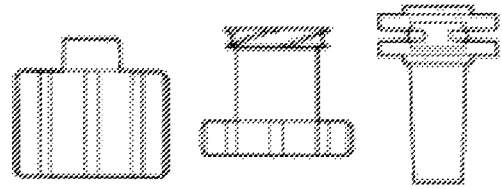
FIGURE 6A
FIGURE 6B
FIGURE 6C

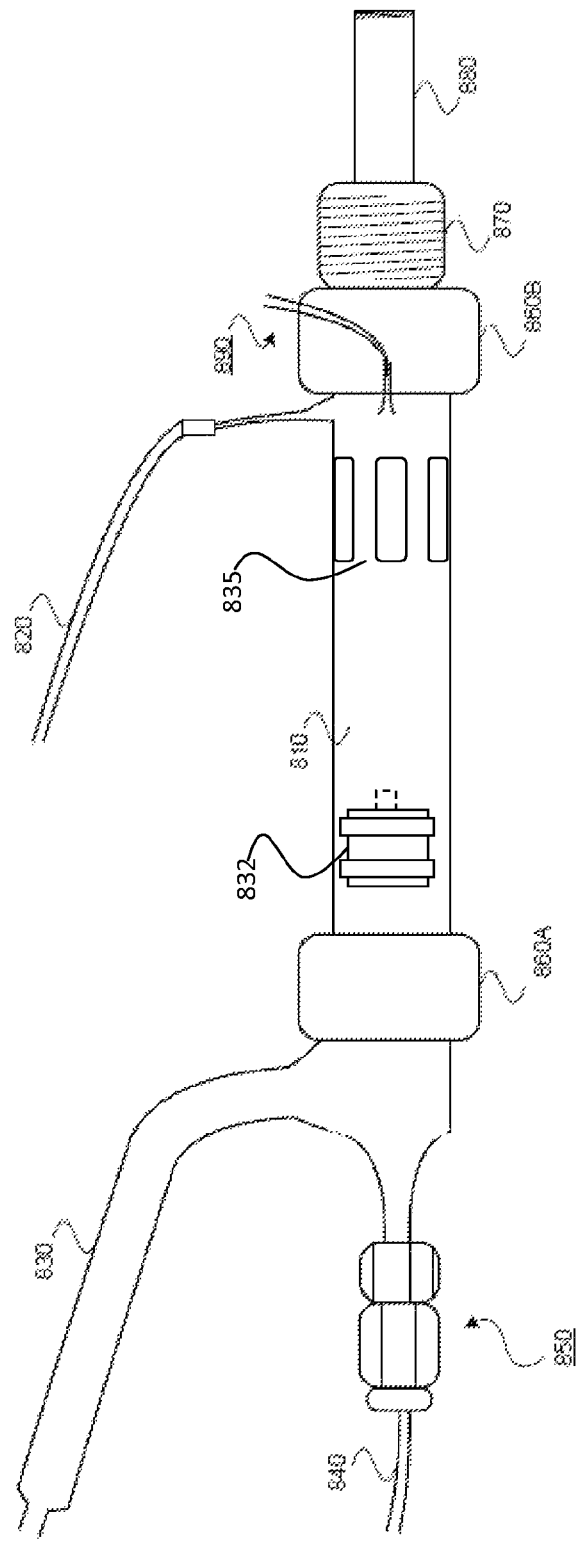

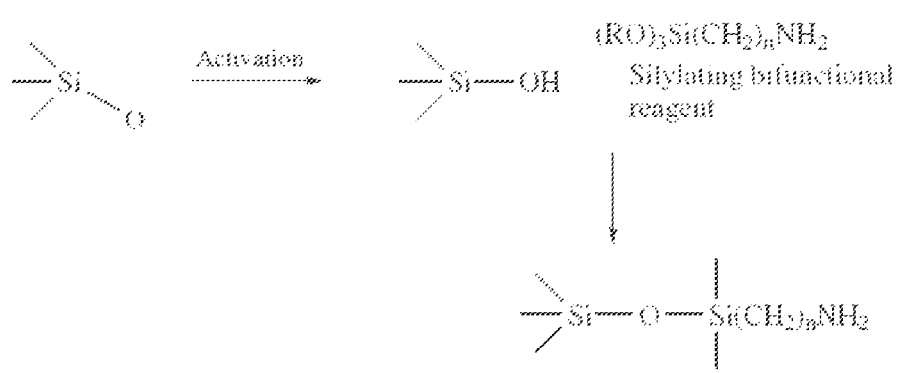
FIGURE 15A
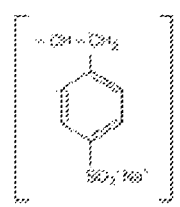 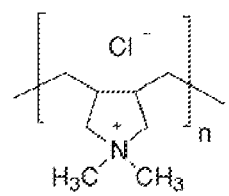
FIGURE 15B  FIGURE 15C

SYRINGE-BASED WHISPERING GALLERY MODE MICRORESONATOR MICROFLUIDIC BIOCHEM SENSOR

§0.2 RELATED APPLICATION(S)

This application claims benefit to U.S. Provisional Application Ser. No. 61/326,098 (referred to as "the '098 provisional" and incorporated herein by reference), filed on Apr. 20, 2010, titled "SYRINGE-BASED WGM SENSOR: HYPODERMIC NEEDLE BASED MICROFLUIDIC WHISPERING GALLERY MODE CHEM-BIO-SENSOR" and listing Stephen ARNOLD and Siyka SHOPOVA as the inventors. The scope of the present invention is not limited to any requirements of the specific embodiments in that application.

§0.1 FEDERAL FUNDING

This invention was made with Government support and the Government may have certain rights in the invention as provided for by the National Science Foundation grant CBET 0933531.

§1. BACKGROUND OF THE INVENTION

§1.1 Field of the Invention

The present invention concerns the use of whispering gallery mode ("WGM") sensors together with a microfluidic device, such as a syringe for example, to detect the presence of, identify the composition of, and/or measure an amount or concentration of substances (referred to generally as "target entities" or "target analytes"), such as chemical or biological entities.

§1.2 Background Information

There exists an ongoing need for sensors for detecting various "target entities" such as, for example, infectious agents (e.g., viruses, bacteria, etc.), toxins, small amounts of proteins, DNA, RNA, etc. Similarly, there exists an ongoing need for sensors for measuring DNA hybridization, protein adsorption, biomolecular mass, etc.

One known device used to detect the presence of small particles is a microsphere sensor coupled to an optical waveguide (e.g., an eroded optical fiber), one end of which is optically coupled with a light source and the other end with a light detector. Whispering gallery modes of the light circulating within the microsphere can be observed in optical signals detected at the detector. Target entities selectively captured (e.g., adsorbed) by target receptors on the surface of the microsphere may shift the whispering gallery modes. These so-called WGM sensors have emerged as an important optical tool for detection and analysis of trace quantities of biological materials. These WGM sensors have been employed in a host of applications including the detection of virus and bacteria, measurement of DNA hybridization and protein adsorption, and biomolecular mass determination.

Examples of such WGM sensors are described in U.S. Pat. No. 7,491,491 (referred to as "the '491 patent" and incorporated herein by reference) and U.S. Pat. No. 7,841,173 (referred to as "the '173 patent" and incorporated herein by reference). Although the '491 and '173 patents mainly describe microsphere-based WGM sensors, such sensors may employ microresonators (referred to generally as "resonators") with geometries other than microspheres, such as, for example, (micro-)cylinders, (micro-)rings, (micro-)disks, (micro-)toroids, (micro-)racetracks, (micro-)bottle resonators, and any other geometry capable of supporting WGM. Each of these configurations relies on the inherent sensitivity of the WGM resonances within the resonator to changes in the external environment to provide a sensitive detection mechanism.

U.S. Patent Application Publication Number US-2010-0297363-A1 (referred to as "the '363 publication" and incorporated herein by reference) describes fabricating more sensitive WGM sensors.

It would be useful to use sensors, such as those introduced above, to test small volumes of fluid. It would be useful to test very small volumes of fluid, such as less than 50 µL for example. It would be useful to test small volumes or very small volumes of body fluids, especially if such testing could be performed contemporaneously with, or shortly after, obtaining the sample of body fluid.

§2. SUMMARY OF THE INVENTION

Embodiments consistent with the present invention may provide a syringe-based whispering gallery mode sensor. Such a sensor may include a syringe provided with an assembly within its needle of the syringe, the assembly including (1) an optical carrier having a reflective distal end, and (2) at least one resonator coupled with the optical carrier. This sensor may be provided in a system including a light source, a light detector, and a data analysis component. A method for determining the presence or concentration of a target substance in body fluid may be performed using such a system.

§3. BRIEF DESCRIPTION OF THE FIGURES

FIGS. 6A-6C illustrates various Luer locks which may be used in a syringe-based WGM sensor consistent with the present invention.

FIG. 8 illustrates a chamber used to fabricate an assembly including an optical fiber and microspheres.

FIGS. 15A-15C illustrate alternative ways to attach a microresonator to an optical fiber.

§4. DETAILED DESCRIPTION

The present invention may involve syringe-based WGM sensors and systems using such syringe-based WGM sensors. The following description is presented to enable one skilled in the art to make and use the invention, and is provided in the context of particular applications and their requirements. Thus, the following description of embodiments consistent with the present invention provides illustration and description, but is not intended to be exhaustive or to limit the present invention to the precise form disclosed. Various modifications to the disclosed embodiments will be apparent to those skilled in the art, and the general principles set forth below may be applied to other embodiments and applications. For example, although a series of acts may be described with reference to a flow diagram, the order of acts may differ in other implementations when the performance of one act is not dependent on the completion of another act. Further, non-dependent acts may be performed in parallel. Also, as used herein, the article "a" is intended to include one or more items. Where only one item is intended, the term "one" or similar language is used. In the following, "information" may refer to the actual information, or a pointer to, identifier of, or location of such information. No element, act or instruction used in the description should be construed as critical or essential to the present invention unless explicitly described as such. Thus, the present invention is not intended to be limited to the embodiments shown and the inventors regard their invention to include any patentable subject matter described.

§4.1 System Components

Figure 1:
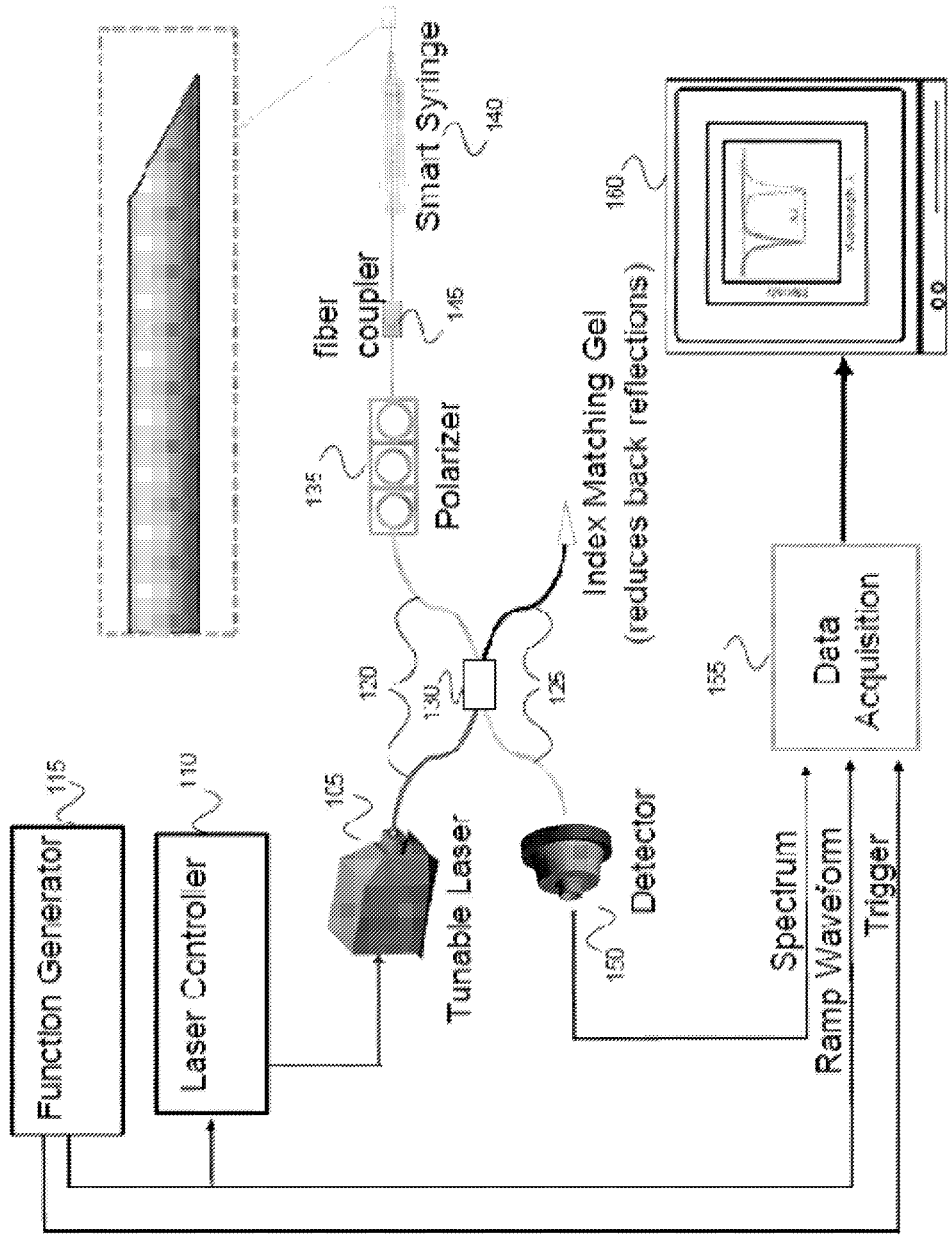
FIG. 1 illustrates an exemplary system, including a syringe-based WGM sensor, consistent with the present invention.

FIG. 1 illustrates a system 100, consistent with the present invention, including a syringe-based WGM sensor 140. The system 100 includes a tunable laser 105, a laser controller 110, a function generator 115, a first waveguide (e.g., an optical fiber) 120, a second waveguide (e.g., an optical fiber) 125, a coupler/splitter 130, a polarizer 135, a syringe-based WGM sensor 140, a fiber coupler 145, a detector 150, a data acquisition component 155 and a display 160.

The tunable laser 105 may be controlled by a laser controller 110, which may be controlled by a function generator 115. The tunable laser 105 outputs light that is provided to the syringe-based WGM sensor 140 via the first waveguide 120, the coupler/splitter 130, the polarizer 135 and the fiber coupler 145. One or more characteristics of the light may change within the syringe-based WGM sensor 140 as will be described in more detail below. Light reflected within the syringe-based WGM sensor (as described in more detail below) may then reach the detector 150 via the fiber coupler 145, and coupler/splitter 130. One or more signals indicative of one or more characteristics of the light received by the detector 150 is output to data acquisition component 155. The data acquisition component 155 may be controlled by one or more control signals from the function generator 115. Finally, the data acquisition component 155 may output signals for rendering on display 160.

Still referring to FIG. 1, the laser controller 110 may be used to tune various parameters of the laser, e.g. current and temperature. Examples of the tunable laser source 105 include but are not limited to distributed feedback lasers and external cavity lasers. The function generator 115 is used to tune the laser in wavelength via various waveforms, e.g. saw tooth wave, sine wave. The first and second waveguides 120 and 125 are the appropriate fiber for the corresponding wavelength of the laser. The coupler/splitter 130 is used to separate the transmitted light from the laser and the reflection returning from the tip of the fiber. The polarizer 135 is used to change to the polarization in order to see resonances more clearly. The fiber coupler (e.g. a SC/SC fiber coupler) 145 is used to make the syringe fiber independent from the main system. The detector 150 is used to capture the spectrum as the laser is tuned. The data acquisition component 155 takes in analog signals from the system in order to display the spectrum accurately and precisely, e.g. ramp voltages and detection transfer voltages. Finally, the display 160 may be used to watch the spectrum in real time and control different operations such as laser temperature.

§4.1.1 Syringe-Based WGM Sensor

Having described an exemplary system 100 and its components, exemplary syringe-based WGM sensors 140 consistent with the present invention are now described. A conventional syringe 200 includes a needle 210, a barrel 220 and a plunger 230. The needle 210 may be fluidly coupled with the barrel 220 (using a Luer lock for example). The plunger 230 fits within the barrel 220 and includes a gasket 235 so that when the plunger 230 is pushed within the barrel 220, contents of the barrel 220 pass through the needle 210 and exit its distal end 215, while if the plunger 230 is pulled within the barrel 220, fluid or gas at the distal end 215 of the needle 210 is drawn through the needle 210 and into the barrel 220. The needle 210, barrel 220 and plunger 230 of the syringe-based WGM sensor 140 may be conventional components. The syringe-based WGM sensor 140 however, may further include the following components.

Figure 3:
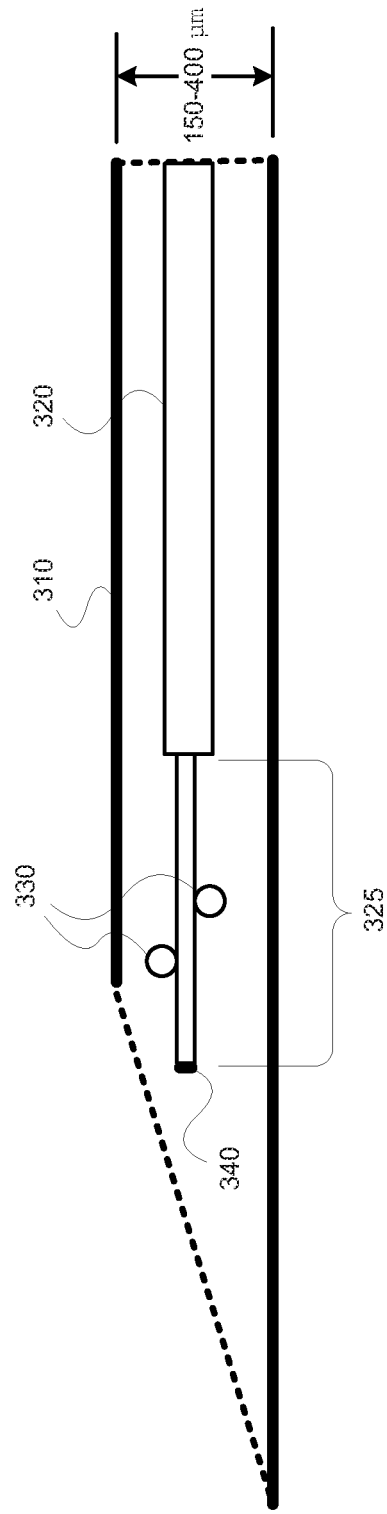
FIG. 3 illustrates a cross-section of syringe-based WGM sensor needle tip, consistent with the present invention.

Referring to FIG. 3, within the needle 310 of an exemplary syringe-based WGM sensor 140, an optical fiber 320 is tapered at its distal end. One or more microresonators (e.g., microspheres 330) are optically (and mechanically and/or chemically) coupled with the tapered portion 325 of the optical fiber 320. The distal end 340 of the tapered portion 325 of the optical fiber 320 is provided with a reflective coating, an example of which is described in more detail below. The needle 310 may have an inner diameter of between 150 and 400 μm.

Figure 4:
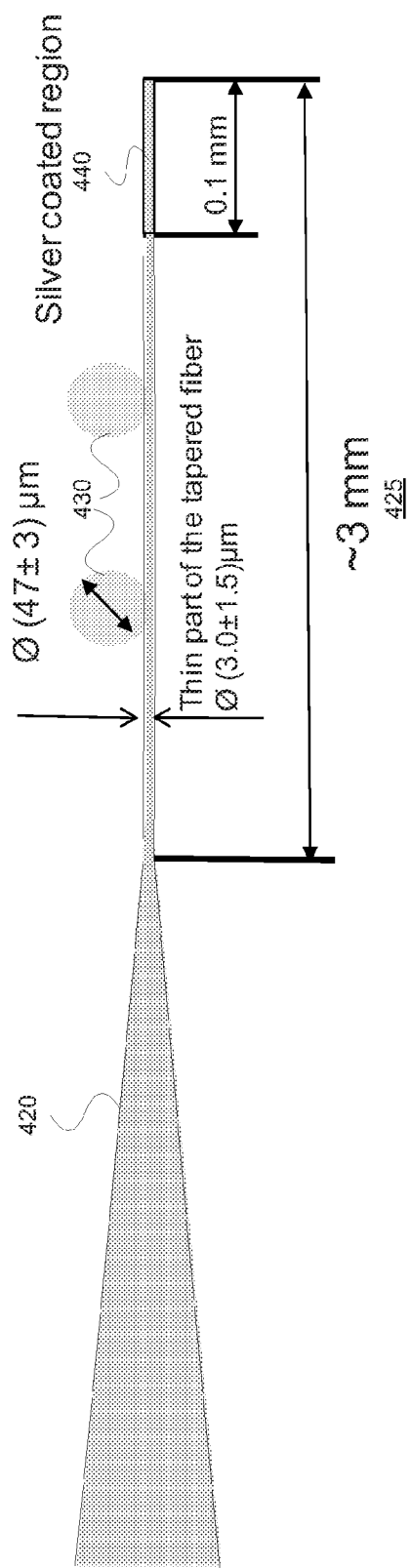
FIG. 4 illustrates a detail of a tapered fiber provided with microspheres and a reflective end region consistent with the present invention.
Figure 5B:
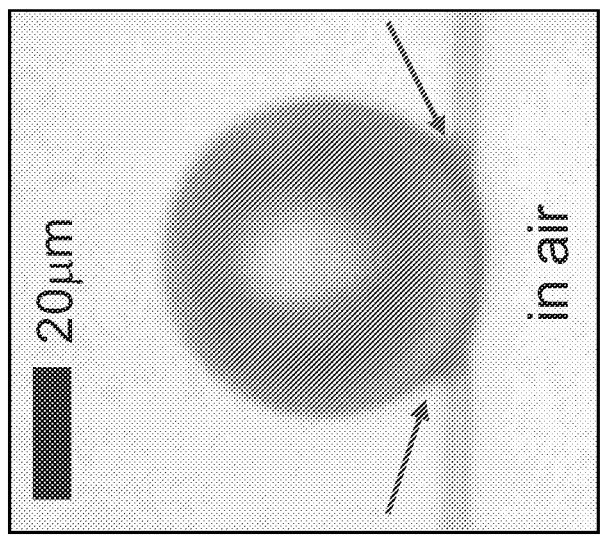
FIGS. 5A and 5B are photomicrographs illustrating the attachment of a microsphere to a tapered fiber in a manner consistent with the present invention.
Figure 5A:
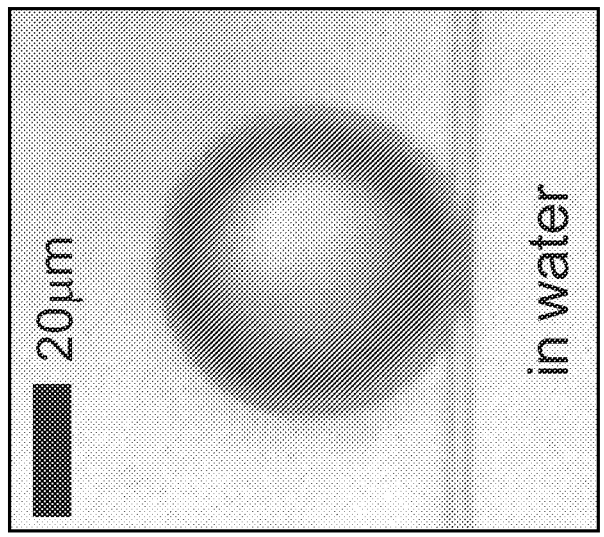

FIG. 4 is a detailed illustration of the tapered portion 425 of an optical fiber 420, such at that provided within an exemplary syringe-based WGM sensor 140. Microspheres 430 are optically (and mechanically and/or chemically) coupled with the tapered portion 425 of the optical fiber 420. FIGS. 5A and 5B are photomicrographs illustrating the adhesion of an approximately 48 μm diameter microsphere 510 to optical fiber 520. The refractive index of the two menisci of adhesive 530 is n=1.33, and is therefore visible in air but not in water. (Compare FIGS. 5A and 5B.) In this example, by applying adhesive to only a small portion of the microsphere 510, most of its surface is left available for sensing (e.g., target adsorption). Referring back to FIG. 4, the distal end 440 of the tapered portion 425 of the optical fiber 420 is provided with a silver coating, which operates to reflect light back through the optical fiber. In this example, the tapered portion 425 of the optical fiber 420 has a diameter of 3.0±1.5 μm and a length of about 3 mm. The silver coated region 440 is about 0.1 mm long. Finally, the microspheres 440 have a diameter of 47±3 μm. The silver coating may be applied to the optical fiber using techniques described in §4.2.2 below. Other techniques to reflect light may be used instead, or in addition.

FIGS. 6A-6C illustrate three (3) exemplary Luer locks, each in side view, end view and cross-sectional side view, which may be used to hold the syringe needle 210 to the barrel 220. Other Luer locks may be used instead. Indeed, the syringe needle 210 can be held or attached to the barrel 220 in other ways.

§4.2 Syringe-Based WGM Sensor Fabrication

In this section, exemplary techniques for attaching the microresonator(s) (e.g., microspheres) to the tapered portion of the fiber are described in §4.2.1, exemplary techniques for providing a reflective coating to the distal end of the tapered portion of the fiber are described in §4.2.2, an exemplary fabrication chamber is described in §4.2.3, and exemplary techniques for providing the assembly within a needle of a syringe are described in §4.2.4 below.

§4.2.1 Exemplary Techniques for Attaching Microresonator(S) to the Tapered Portion of the Fiber In this section, exemplary techniques for attaching microspheres to the tapered portion of an optical fiber are described. The present invention is not limited to the techniques described here, nor is it limited to the resulting assembly. Microspheres may be coupled to optical fiber using the techniques discussed in the article J. C. Knight, G. Cheung, F. Jacques, and T. A. Birks, "Phase-Matched Excitation of Whispering-Gallery-Mode Resonances by a Fiber Taper," *Opt. Lett.*, 22, pp. 1129-1131 (1997) (incorporated herein by reference). (The article Ying-Zhan Yan, Chang-Ling Zou, Shu-Bin Yan Fang-Wen Sun, Zhe Ji, Jun Liu, Yu-Guang Zhang, Li Wang, Chen-Yang Xue, Wen-Dong Zhang, Zheng-Fu Han, and Ji-Jun Xiong, "Packaged Silica Microsphere-Taper Coupling System for Robust Thermal Sensing Application", *Optics Express*, Vol. 19, No. 7, 5753 (2011) concerns coupling microspheres to fiber. However, it pertains to a temperature sensor and the sphere is completely covered by glue, which makes it insensitive for adsorption sensing.)

One or more polystyrene microspheres of nominal diameter of 45.0 micrometers (Polyscienses Inc. micrometers—catalog #07314) can be attached to a silica fiber (FIS-250UM 9/125 SM FC/UPC). The intermolecular forces between polystyrene and fused silica are weak. Consequently, an adhesive is used for robust attachment. In addition, to minimize losses, the adhesive material should "disappear" optically in water (or the solution or solvent (fluid) being tested). Fluorinated polymers are known to have low refractive index close to that of water. (See, e.g., the article, W. Groh and A. Zimmermann, "What Is the Lowest Refractive Index of an Organic Polymer," *Macromolecules* 24, 1991 (incorporated herein by reference). These adhesive materials can bond to both the silica fiber (e.g., through possible hydrogen bonds) and the polystyrene microsphere (e.g., by Van der Waal's interactions). An exemplary adhesive suitable to attach microspheres to the fiber is a fluorinated acrylated/methacrylated polymer, synthesized by Ovation Polymers (Medina, Ohio) and catalogued as UV-Opti-Cladd1.33TL.

The adhesive may be cured through UV photopolymerization, under nitrogen atmosphere, using a 100 mW UV LED at 365 nm.

The inventors have attached polystyrene microspheres (~45 um) to the thin part (~3 um) of a single tapered silica optical fiber with sufficient strength for use in water or other biological aqueous solutions. The polystyrene sphere solution was obtained from the original solution (Polyscience-cat #07314) by 50-fold dilution with DI water. Depending on the need, several droplets of the diluted solution were added onto a clean polymethyl methacrlyate (PMMA) plate. Each droplet with 20 uL of diluted solution was prepared on the PMMA plate. The PMMA plate was put into vacuum chamber until the water was vaporized. Three (3) fibers were used to deposit the microspheres, using a procedure that provides accurate and precise control of microsphere attachment under microscope by x,y,z translational stages.

A tapered silica fiber (the waveguide fiber) is prepared by heating and pulling a standard optical fiber. The tapered portion of the silica fiber is then carefully cut, using a precision fiber cleaver, at 90 degrees with respect to the axes of symmetry (optical axis) of the fiber. The fiber is then treated (e.g., plasma treated, e.g., for 20 minutes) to remove possible contamination introduced during the fiber pulling process and also to enhance the hydrophilicity of the silica fiber surface. This is followed by coating the fiber with a thin layer of ethanol. (This coating treatment increases the chance of picking up polystyrene microspheres from PMMA plate.) Polystyrene microspheres are transferred from the PMMA substrate onto a thick part of the fiber close to the tapered region.

A second fiber is dipped into an adhesive solution. This second fiber is used to apply the adhesive onto the thin part of the target fiber as stated above. Small adhesive pads are formed to the thin area (~3 um diameter) where the microspheres were about to be placed.

Finally, the third fiber is used to transfer precisely, the microspheres from the thick part of the fiber to the desired locations defined by the small adhesive pads on the tapered part of the fiber. The third fiber is also used to depress each of the microspheres against the target fiber such that extra adhesive between the microsphere and the fiber is forced out.

To cure this assembly, the air in the cell is replaced with nitrogen gas, and the adhesive is exposed to UV light (wavelength of 365 nm) for 15 min.

Figure 7B:
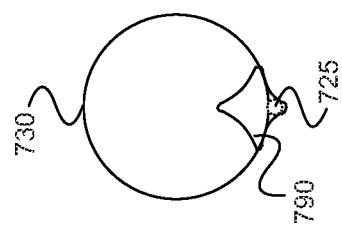
FIGS. 7A and 7B are side and end views, respectively, illustrating a microsphere adhered to a tapered optical fiber.
Figure 7A:
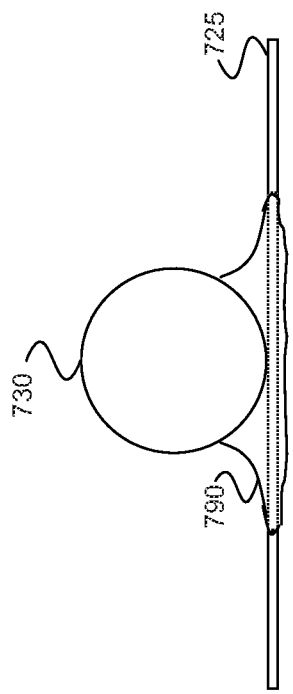

The attached sphere on fiber is shown in FIGS. 7A and 7B. More specifically, FIG. 7A is a side view, and FIG. 7B is an end view, of the polystyrene microsphere 730 coupled with a tapered portion 725 of an optical fiber using adhesive 790.

After the microsphere(s) is attached, the assembly may be tested to ensure adequate WGM coupling.

To reiterate, in this section, exemplary techniques for attaching microspheres to the tapered portion of an optical fiber were described. The invention is not limited to the techniques described here, nor is it limited to the resulting assembly.

§4.2.2 Exemplary Techniques for Providing a Reflective Coating to the Distal End of the Tapered Portion of the Fiber In this section, exemplary techniques for providing a reflective coating to the distal end of the tapered portion of an optical fiber is described. The present invention is not limited to the techniques described here, nor is it limited to the resulting assembly. Techniques from the article, S. Q. Wang, "Silver-Coated Near Field Optical Scanning Microscope Probes Fabricated by Silver Mirror Reaction," *Appl. Phys.*, B 92, 49-52 (2008) (incorporated herein by reference) may be used for example.

The cut fiber end is coated with silver to enhance the reflection of the signal. The precise cleaving of the fiber end (at 90 degrees to the optical axis of the fiber) is important to obtain a good reflection signal. The cleanliness and accurate flatness of the fiber end affect the uniformity and binding strength of the silver layer. Plasma cleaning (e.g., for 20 minutes) is performed before the silver coating process. Then, the cleaved fiber end is dipped in 10% sodium hydroxide solution before silvering process.

The silver solution is prepared by adding 1.5 mL $AgNO_3$ (1.0 M) and 0.1 mL $NH_3.H_2O$ (25%-28%). The solution is mixed well until a brownish precipitation disappears. Then, 0.1 mL glucose (2.26M) is added. The total coating solution volume is 1.7 mL.

The silver coating is done on a controlled stage monitored by a camera with a 10× objective lens. First, 0.5 mL of the coating solution is added to 1 mL cuvette. The single tapered fiber with spheres is held in a fiber chuck with controlled vertical movement. The cuvette is fixed on a holder also with z movement. In this way, the length of the fiber's coated region can be well controlled. The reaction resulting in the silver coating of the fiber end takes about 1 hour without heating. The reaction is considered to be complete when the silver is observed to have coated inside surface of the cuvette.

§4.2.3 Exemplary Fabrication Chamber

FIG. 8 illustrates an exemplary chamber 800 for use in fabricating the assembly of fiber and microspheres. More specifically, the chamber 800 includes a glass cavity 810, outlet port 820, inlet port 830, a multi-mode guide 832, a flat viewing window 835, a multimode optical fiber for detection of scattered light from the resonator for alignment purposes during fabrication 840, Swagelock fitting 850, holders 860, friction lock ring 870, industry standard fiber chuck 880 holding the tapered fiber and thermistor 890. An exemplary glass cavity 810 may hold about 6 mL of liquid/gas, have a length of about 4 inches and an inside diameter of about 0.37 inches. The inlet and outlet ports 820/830 may be used to fill and/or purge the chamber with Nitrogen (which may be used during a UV curing of the adhesive, and may also be used to test the sensor. The thermistor 890 may be used for local measurement of temperature. Note that although the exemplary chamber 800 enables the fiber-microsphere assembly to be fabricated and tested, it includes features related to laboratory experimentation which might not be necessary to produce suitable assemblies.

§4.2.4 Exemplary Techniques for Providing the Assembly in a Syringe

Referring back to FIG. 2, in one embodiment consistent with the present invention, the assembly is provided such that the tapered end of the fiber is accommodated within the needle 210 and the fiber extends through the barrel 220 and exits the top of the barrel. In such an embodiment, the fiber may be adhered to the inside surface of the barrel 220 at one or more places. The fiber is thin enough so that the plunger 230 can still freely move within the barrel 230 and such that the gasket 235 can still form a seal. In some refined embodiments, the fiber may be embedded within the wall of the barrel 220, or may sit within a groove in the inside wall of the barrel 220.

Figure 2:
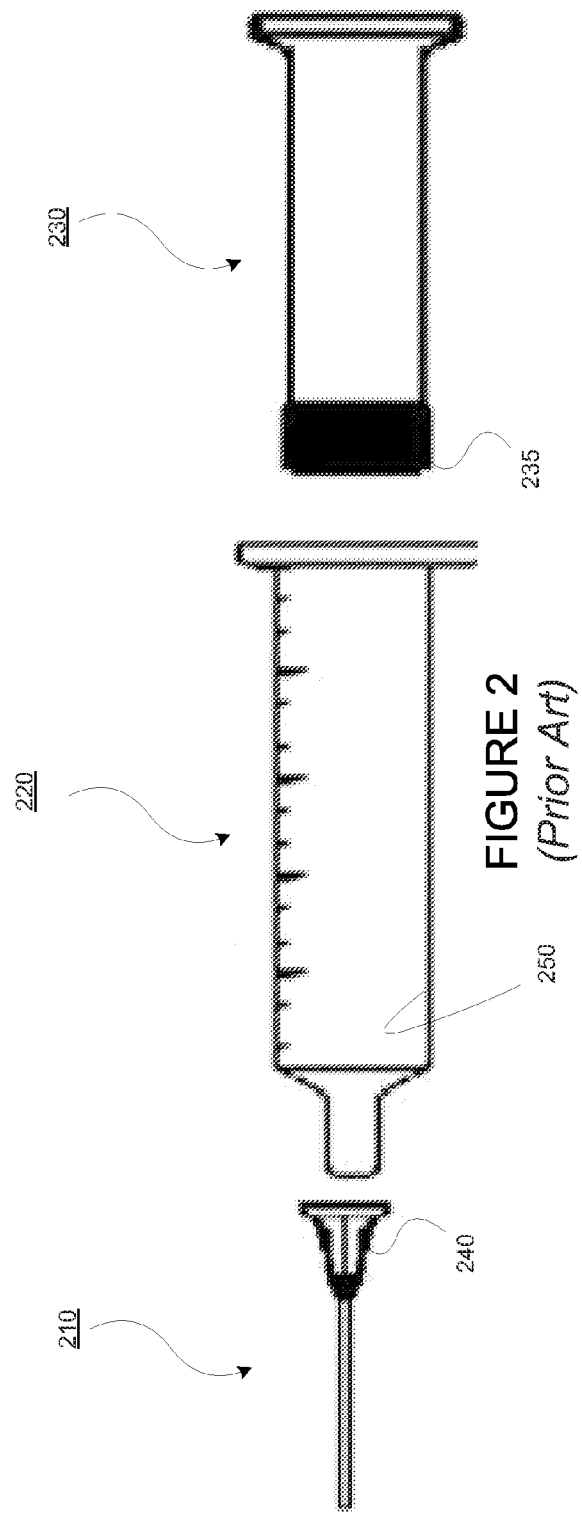
FIG. 2 illustrates parts of a known hypodermic syringe.

Still referring to FIG. 2, in some exemplary embodiments consistent with the present invention, the fiber may exit from an opening in the Luer lock 240 (or some other fitting at the proximal end of the needle 210). In this way, the fiber need not be provided within the barrel 220.

Referring to both FIGS. 1 and 2, in some exemplary embodiments consistent with the present invention, the fiber coupler 145 may be built into the syringe barrel 220, or may be built into the Luer lock 240 (or some other fitting at the proximal end of the needle 210).

§4.3 Using System Including a Syringe-Based WGM Sensor

One skilled in the art will understand how to use the system 100 in view of the '491 patent, the '173 patent, and the '363 publication, all of which have been incorporated herein by reference.

Figure 9A:
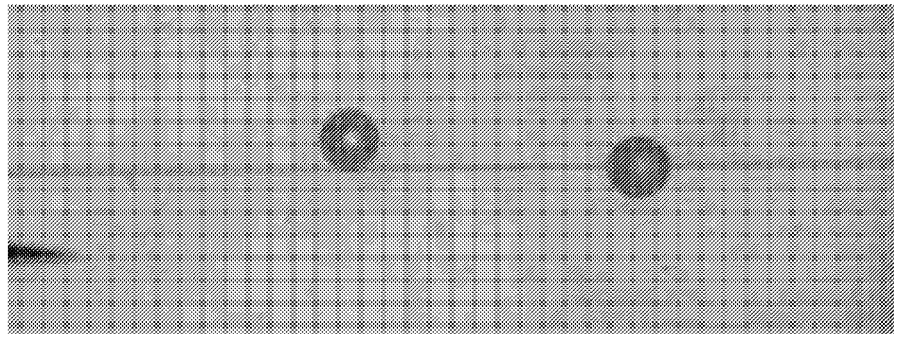
FIGS. 9A and 9B are photomicrographs illustrating the excitation of light in microspheres provided on a tapered fiber.
Figure 9B:
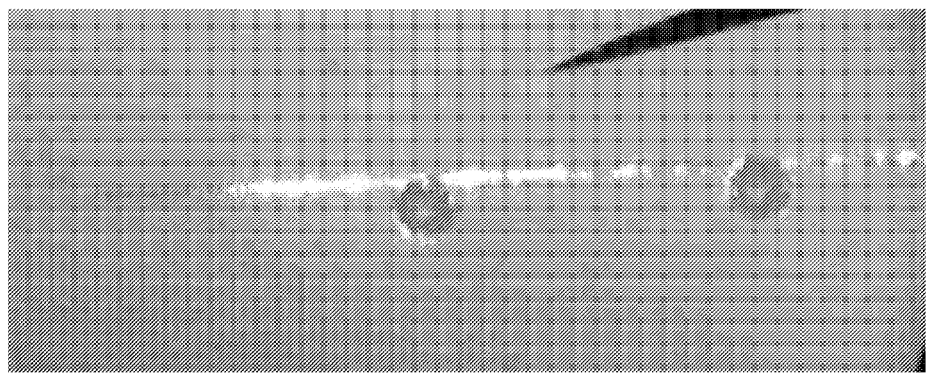

FIGS. 9A and 9B are photomicrographs illustrating the assembly 900 of two microspheres on the tapered end of an optical fiber. In this example, one of the microspheres is functionalized differently so that it will be insensitive to the target, but will provide a reference for the sources of noise, such as changes in temperature, the refractive index of the surrounding solvent, etc. FIG. 9A illustrates the assembly 900 without light being applied. In FIG. 9B, laser light is transmitted through the fiber and excites a WGM resonance within the microspheres. Light is reflected back into the fiber core from a silver coating at the end of the fiber.

Figure 10:
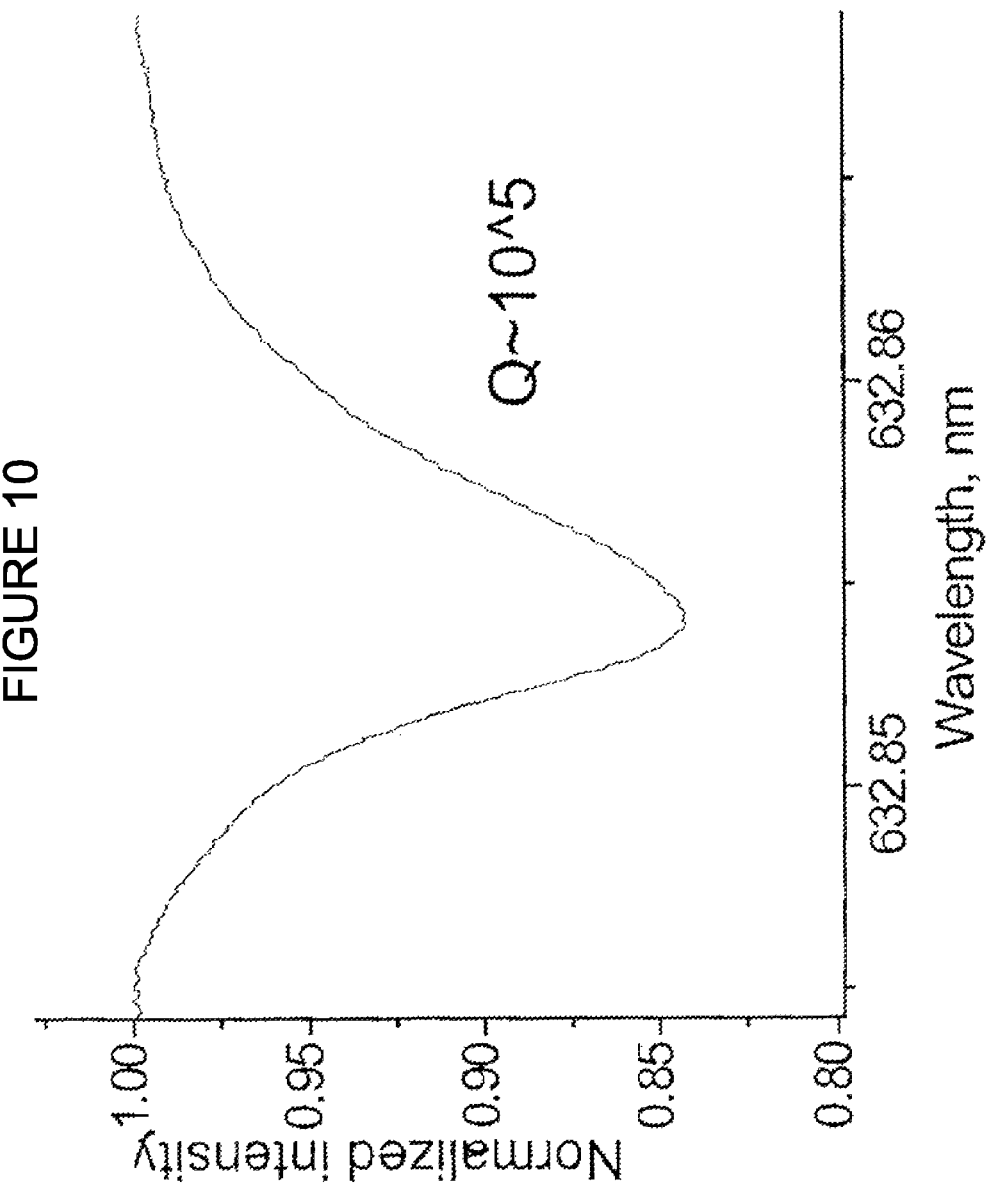
FIG. 10 illustrates the resonance of a plain 20 micron radius (40 micron diameter) microsphere attached to a quartz fiber.
Figure 11:
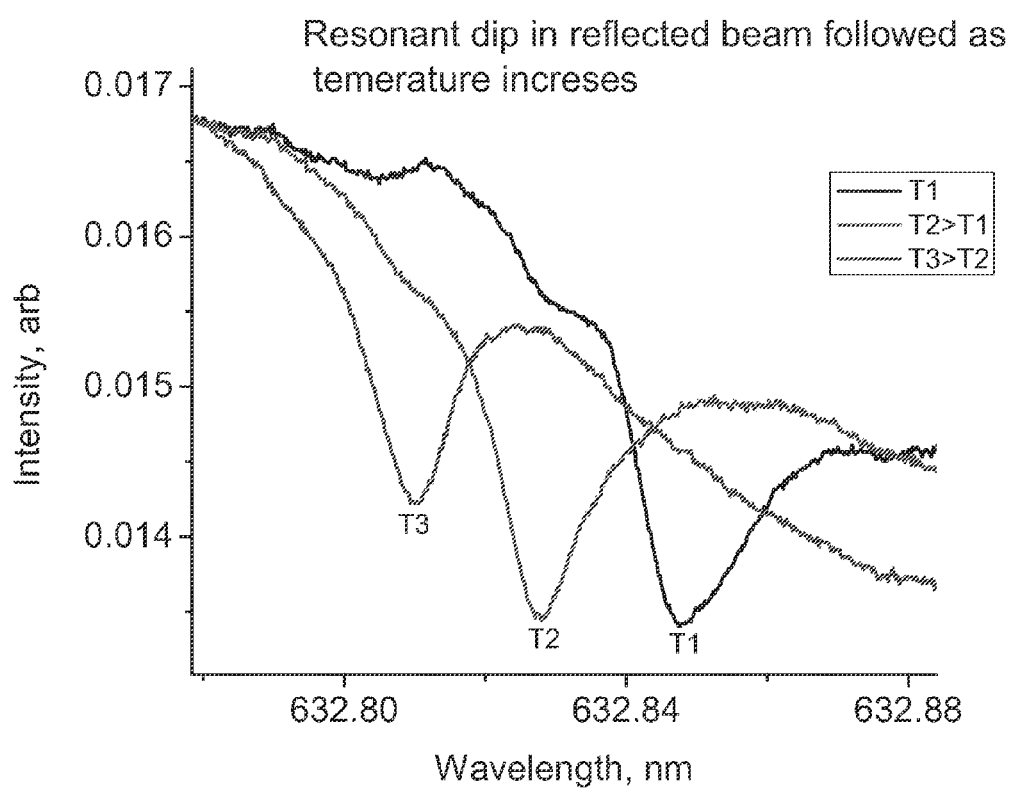
FIG. 11 illustrates the affect of temperature on the resonance of a microsphere.

FIG. 10 illustrates a dip in transmitted power through the fiber, at about 632.855 nm, when a microsphere of about 40 μm is attached. The Q-factor is on the order of $10^5$. FIG. 11 illustrates the affect of temperature on the dip in transmitted power through the fiber. In this graph, T1<T2<T3. As can be seen, the dip and transmitted power occurs at decreasing wavelengths for increasing temperatures. Note that the detected signal was reflected from the silvered end of the fiber and separated from the incident beam by the coupler/splitter.

Figure 12:
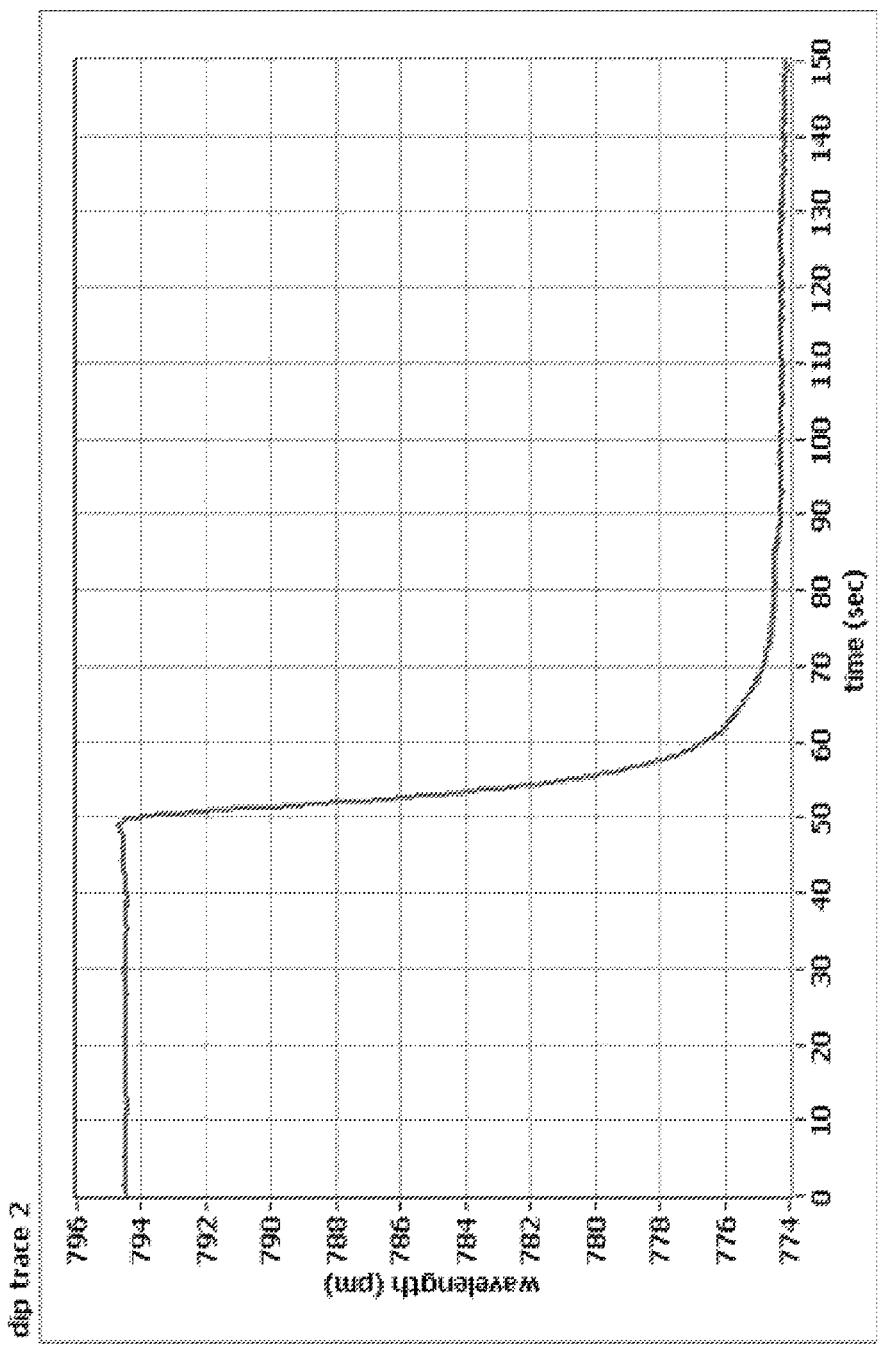
FIG. 12 illustrates the change in wavelength of a microsphere in 0.25 M NaCl solution, subsequently washed with DI $H_2O$.

FIG. 12 illustrates the detection of a change in refractive index of the surrounding medium (that is, a change from salt water to fresh water). A polystyrene microsphere having a diameter of 45±1 μm is permanently attached to a tapered fiber and excited into WGM with a laser light transmitted through the fiber. The assembly is initially provided in 0.25 M NaCl, but is washed with DI $H_2O$ at about 50 seconds. The corresponding change in wavelength from about 794 to about 774 μm is observed.

Figure 13:
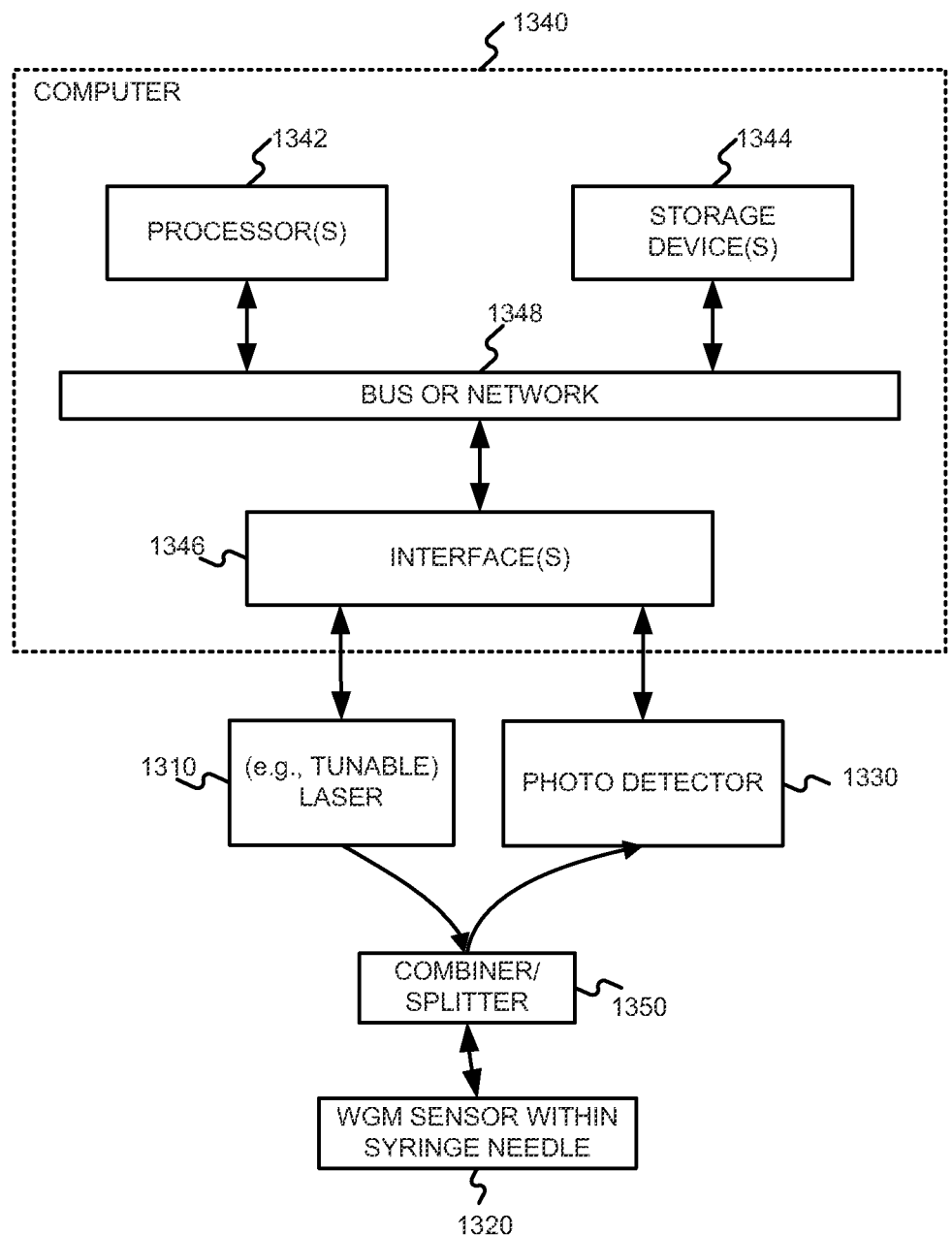
FIG. 13 is a simplified block diagram of a system in which a syringe-based WGM sensor may be used.

FIG. 13 is a simplified block diagram of exemplary sensor detection system 1300 which may use a syringe-based WGM sensor 1320 for detecting and/or identifying target entities such as biomolecules (e.g. proteins, virus particles, etc.). The sensitivity of the WGM sensor 1320 may have been enhanced (e.g., using the techniques described in the '363 publication) such that single protein or other small entity detection and identification are possible.

Sensor detection system 1300 may include a laser 1310, a syringe-based WGM sensor 1320, an optical detector, such as a photo detector 1330, a computer system 1340 and a combiner/splitter 1350. The computer system 1340 includes at least one processor 1342, at least one storage device 1344 (e.g., RAM, ROM, flash memory, computer readable storage medium, etc.), at least one interface 1346, and at least one bus or network 1348 over which the various elements may interchange data and information.

The tunable laser 1310 may be controlled to emit light (of an appropriate wavelength and intensity) into the syringe-based WGM sensor 1320. The photo detector 1330 may detect light reflected back from the syringe-based WGM sensor 1320, via the combiner/splitter 1350. The evaluation of changes in signal output from photo detector 1320 may be used to determine the existence of, or the amount of, a target entity that is received by the target receptors provided on the syringe-based WGM sensor 1320. In systems 1300 including a computer 1340, the processor(s) 1342 under the direction of routines in memory 1344, may control the laser 1310 through an interface(s) 1346. The processor(s) 1342 may receive output signaling from photo detector 1330 through an interface(s) 1346 and process the signaling to determine the existence, and/or amount, of the target entity sensed.

The syringe-based WGM sensor 1320 may have any of a number of possible configurations including a single microresonator assembly, a multiple microresonator assembly using different receptors on different microresonators, and a multiple microresonator assembly including at least one microresonator without receptors to be used to characterize and remove common mode noise. (See, e.g., the '173 patent.)

In some embodiments, the sensor detection system 1300 may be implemented using one or more modules. Such modules may be implemented using software, hardware, or a combination of software and hardware.

Figure 14:
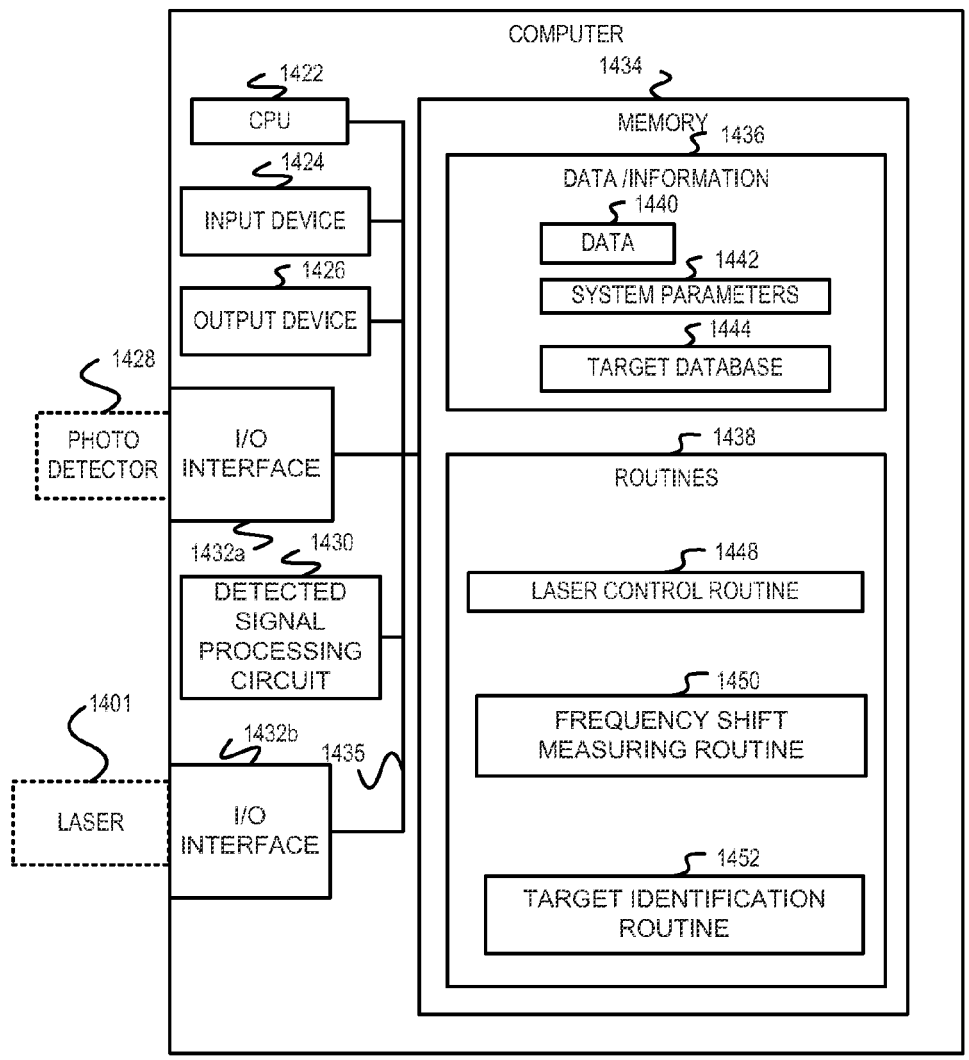
FIG. 14 is a block diagram of a computer which may be used in the system of FIG. 1 or FIG. 13.

FIG. 14 illustrates an exemplary computer system 1400 which may be used in the system 1300. The computer 1400 may interface with a tunable narrow linewidth (<1 MHz) laser (such as, for example, a distributed feedback ("DFB") laser, a distributed Bragg reflector ("DBR") laser, an external cavity laser ("ECL"), a fiber laser, laser light due to harmonic generation or optical parametric generation ("OPG") including, but not limited to, second harmonic generation ("SHG"), sum frequency generation ("SFG"), difference frequency generation ("DFG"), etc.) 1401 and an optical detector (e.g., a photo detector 1428), each of which may be coupled with the computer 1406 through I/O interface 1432. (The combiner/splitter and syringe-based WGM sensor are not shown.) The laser 1401 may be, e.g., a green diode laser with external cavity operating at a wavelength of about 530 nm (or a red, 600-800 nm external cavity laser), also generally available lasers having a wavelength of about 1.3 or 1.6 μm, external cavity (e.g., diode) lasers with a wavelength of 1060 nm, etc. Generally, a shorter wavelength (e.g., visible light) is better because absorption of the resonant light by the surrounding medium may degrade the quality of the resonance and reduce the system sensitivity. However, there is a trade-off in the extent to which the short wavelength field permeates the surrounding medium. This reduced reach of the short wavelength source may limit the extent to which the light force may draw target receptors towards to the surface of the microresonator. The laser 1401 selected may operate at a wavelength including, but not limited to, the foregoing wavelengths. Other wavelengths may be used, perhaps in concert with other sensor design changes.

The photo detector 1428 may provide data to a computer system 1400 through I/O interface 1432. In some embodiments the photo detector 1428 may be included as part of the computer system 1400. The computer system 1400 may include a processor (e.g., a CPU) 1422, an input device 1424, an output device 1426, a detected signal processing circuit 1430, I/O interfaces 1432a,b, and memory 1434 coupled together via bus or network 1435 over which the various elements may interchange data and information. Memory 1434 may include data/information 1436 and routines 1438. Data/information 1436 may include data 1440, system parameters 1442, and target entity information 1444. Routines 1438 may include a laser control routine 1448, a frequency shift measurement routine 1450, and/or a target identification routine 1452. The processor 1422 may be used to execute the routines 1438 and use the data/information 1436 in memory 1434 to detect and identify substances such as biomolecules (e.g., proteins or virus particles, etc.). The input device 1424 may include keyboards, keypads, etc., and may be used to notify the computer system 1406, that a sample has been drawn into the needle 210. Output devices 1426 may include displays, printers, speakers, etc., detected frequency shifts, and identified target entities 1420.

The computer system 1400 may operate as follows. Photo detector 1428 receives the light transmission from the laser 1401 (which has been altered by the resonant modes of WGMs of the syringe-based WGM sensor (not shown), shifts in resonant mode due to adsorbed target entities 420, and reflected back) and converts the optical signal to an electrical signal. Detected signal processing circuit 1430 receives the electrical signal from the photo detector 1428 and detects such resonance modes (manifested as dips in the transmitted signal which correspond to resonant modes). I/O interface 1432 may include line drivers and receivers, A/D converters, D/A converters, frequency counters, etc. Data 1440 may include data collected on the transmitted signal, e.g., frequency, detected resonant modes, shifts detected in resonant modes, etc.

System parameters 1442 may include frequency and intensity of the laser 1401, radius of the microresonator (not shown), parameters defining a specially treated target reception region on the microresonator (not shown), index of refraction of the microresonator (not shown), index of refraction of the aqueous medium (e.g., blood or other body fluid, not shown), thermal models, and calibration parameters. Target entity information (e.g., in the form of a database) 1444 may include look-up tables associating step changes or level shifts in the frequency of the modes observed with specific target entities 1420 (e.g., protein molecules such as thyroglobulin, ferritin, or virus particles such as lambda phage). Laser control routine 1448 may control and monitor the tunable DFB laser 1401 to maintain a detectable WGM signal at the photo detector 1428 and provide current precise laser frequency information to the computer system 1406. Frequency shift measuring routine 1450 processes information from the detected signal processing circuit 1430 to detect step changes of shifts in mode frequencies with time. Target identification routine 1452 uses the output of the frequency shift measuring routine 1450 to match the step level changes to a corresponding target entity, e.g., a specific protein molecule or virus particle such as a lambda phage virus particle.

The tunable laser 1401 is optically coupled with the microresonator (not shown), and the photodetector 1428 via optical waveguides and combiner/splitter (not shown). This allows light being transmitted from the laser 1401 to the photodetector 1428 to be coupled into a WGM of the microresonator (not shown), create detectable resonant modes in the transmission, and create detectable frequency shifts in the resonant modes in response to adsorbed target entities on the microresonator (not shown). In other embodiments, the light from the laser 1401 is coupled into the microresonator (not shown) via means other than a physically continuous optical waveguide such as, for example, via lenses, splitters, etc.

§4.4 Refinements, Alternatives, and Extensions

Although exemplary embodiments consistent with the present invention describe fabricating microsphere sensors, other configurations of WGM sensors such as, for example, (micro-)cylinders, (micro-)disks, (micro-)rings, (micro-) racetrack, (micro-)bottle resonator and (micro-)toroids (or any other resonator geometry that can support a WGM) may be used.

Although the resonator was described as being silica, other materials for a resonator such as amorphous sapphire, glass, silicon, silicon nitride, silicon oxynitride, gallium nitride (GaN), gallium arsenide (GaAs), indium arsenide (InAs), etc., may be used in a manner consistent with the present invention. Various chemical processes, known to those skilled in the art, may be performed to allow the attachment of target receptors to the resonator.

Although some exemplary embodiments described above used a tapered optical fiber to evanescently couple light to the microresonator, other optical waveguides (such as, for example, eroded fiber, lithographed waveguide, rib waveguides, channel waveguides, nanowires, and other structures (or media) capable of supported a guided wavemode) may be used instead. However, such waveguides, together with any attached microresonators, must be able to fit within the diameter of the syringe needle 210 (or alternatively, within the syringe barrel 220) being used.

In at least some exemplary embodiments consistent with the present invention, the microresonator may have a diameter of between 100 μm or less, and preferably 30-50 μm though resonators having other diameters may be used, provided that such microresonators can fit, together with any attached waveguide, within the diameter of the syringe needle 210 (or alternatively, within the syringe barrel 220) being used. Although some exemplary fabrication methods used adhesive to attached microspheres (or some other microresonators) to an optical fiber, other attachment techniques, such as chemical attachment may be used. For example, FIG. 15A illustrates APTES (n=2) on fiber and sulphonated or carboxylated units on Polystyrene (PS). An aminated PS bead is attracted to ionized silanol groups on silica fiber surface. Assembly is simply a matter of "fishing" with the silica tip. As shown in FIGS. 15B and 15C, it is possible to use thin layers of two different types of polyelectrolyte on the surface of the fiber and PS microsphere respectively, which will leave positive charge on one surface and negative on the other. Therefore, the two surfaces will come in contact by electrostatic attraction. Van der Waals forces will also contribute to this bonding. The two types of electrolytes that have similar strength and have been used for multilayer deposition are poly(diallyldimethylammonium chloride) (PDAC; Aldrich; MW 150 000—leaves positive charge after washing the Cl ions) and sulfonated polystyrene (SPS; Polysciences; MW 35 000—leaves negative charge after washing the Na ions).

"Target receptor" is meant to describe any bionanoparticle or macromolecule (e.g., virus, protein, polynucleotide, polysaccharide, etc.) that can be attached to a micro resonator and receive a target entity of interest. Target receptors are intended to include numerous bionanoparticles and chemical classes, but will typically be organic molecules, or small organic compounds. Target receptors may include any functional groups (e.g., an amine, a carbonyl, a hydroxyl, a carboxyl group, sulfonyl, etc.) necessary for structural interaction (e.g., covalent bonding, hydrogen bonding, etc.) with target entities (e.g., proteins, antibodies, virus, etc.). Target receptors may include, for example, cyclical carbon or heterocyclic structures and/or aromatic or polyaromatic structures substituted with one or more of the above functional groups. Thus, target receptors may include biomolecules such as proteins, peptides, nucleic acids, saccharides, fatty acids, steroids, purines, pyrimidines, derivatives, and structural analogs or combinations thereof. Note that in some instances, target receptors are not needed, provided that a force caused by the WGM in the resonator is sufficient to attract the target of interest to the resonator.

Target receptors can be obtained from a wide variety of sources including, for example, libraries of synthetic or natural compounds. Numerous means are available for random and directed synthesis of a wide variety of organic compounds and biomolecules, including expression of randomized oligonucleotides. Alternatively, libraries of natural compounds in the form of bacterial, fungal, plant and animal extracts are available to, or readily produced by, those skilled in the art. Additionally, natural or synthetically produced libraries and compounds may be modified through conventional chemical, physical and biochemical means. Known pharmacological agents may be subjected to directed or random chemical modifications, such as acylation, alkylation, esterification and/or amidification to produce structural analogs.

In some embodiments consistent with the present invention, the laser wavelength is 1060 nm, and has a drive power as little as 42 µW and as much as 1 mW. Naturally, other laser wavelengths and drive powers may be used.

As used in this application (and as generally understood in the art), a "protein" includes at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids in the context of this application.

The target receptors may be naturally occurring proteins, or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the systems described herein. Particularly preferred in this embodiment are libraries of bacterial, fungal, viral, and mammalian (e.g., human) proteins.

In at least some embodiments consistent with the present invention, the target receptors are peptides. The peptides may be digests of naturally occurring proteins as is outlined above, random peptides, or "biased" random peptides. "Randomized" means that each nucleic acid and peptide consists essentially of random nucleotides and amino acids, respectively. These random peptides (or nucleic acids) may be chemically synthesized, and therefore may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In at least some embodiments consistent with the present invention, the target receptors may be nucleic acids. "Nucleic acid" or "oligonucleotide" means at least two nucleotides covalently linked together. A nucleic acid will generally contain phosphodiester bonds, although in some cases, as outlined below, nucleic acid analogs are included that may have alternate backbones, comprising, for example, phosphoramide, phosphorothioate, phosphorodithioate, O-methylphophoroamidite, and peptide nucleic acid backbones and linkages. Other analog nucleic acids include those with positive backbones, non-ionic backbones and non-ribose backbones. Nucleic acids containing one or more carbocyclic sugars are also included within the definition of nucleic acids. The ribose-phosphate backbone may be modified to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and basepair analogs such as nitropyrrole and nitroindole, etc.

As described above generally for proteins, nucleic acids may be naturally occurring nucleic acids, random nucleic acids, or "biased" random nucleic acids. For example, digests of procaryotic or eukaryotic genomes may be used as is outlined above for proteins.

In general, the target receptors are designed to be complementary to a target entity, such that hybridization of the target entities and the target receptors occurs. It is not necessary for this complementarity to be perfect. For example, in the context of nucleic acid sequences, there may be one or more base pair mismatches that will interfere with hybridization between the target entity and the target receptor. However, if the number of mutations is so great that no hybridization can occur under even the least stringent of hybridization conditions, the target entity will not be considered to be complementary to the target receptor. "Substantially complementary" means that the target receptors are sufficiently complementary to the target entities to hybridize under selected reaction conditions.

In some embodiments consistent with the present invention, the target entity may be a "target sequence" which is a nucleic acid sequence on a single strand of nucleic acid. The target sequence may be a portion of a gene, a regulatory sequence, genomic DNA, cDNA, RNA including mRNA and rRNA, etc. The target sequence may be any length, with the understanding that longer sequences are more specific. As will be appreciated by those skilled in the art, the complementary target sequence may take many forms. For example, it may be contained within a larger nucleic acid sequence (e.g., all or part of a gene or mRNA, a restriction fragment of a plasmid or genomic DNA, among others.) Target receptors are made to hybridize to target sequences to determine the presence or absence of the target sequence in a sample.

In at least some embodiments consistent with the present invention, the target receptors may be organic chemical moieties.

In some embodiments consistent with the present invention, linkers may be used to attach the target receptors to the resonator, to facilitate good attachment, provide sufficient flexibility to allow good interaction with the target entities, and/or to avoid undesirable binding reactions.

In at least some embodiments consistent with the present invention, the bioactive target receptors are synthesized first, and then covalently attached to the resonator. As will be appreciated by those in the art, this will be done depending on the composition of the bioactive target receptors and the resonator. The functionalization of solid support surfaces such as certain polymers with chemically reactive groups such as thiols, amines, carboxyls, etc., is generally known in the art. Accordingly, "blank" resonators may be used that have surface chemistries that facilitate the attachment of the functionality desired. Some examples of these surface chemistries for blank microspheres include $NH_2$ (Amine), COOH (Carboxylic Acid), CHO (Aldehyde), $CH_2$—$NH_2$ (Aliphatic Amine), CO $NH_2$ (Amide), $CH_2$—Cl (Chloromethyl), CONH—$NH_2$ (Hydrazide), OH (Hydroxyl), $SO_4$ (Sulfate), $SO_3$ (Sulfonate), and Ar $NH_2$ (Aromatic Amine). These functional groups can be used to add any number of different bioactive agents to the resonator, generally using known chemistries. For example, bioactive target receptors containing carbohydrates may be attached to an amino-functionalized support; the aldehyde of the carbohydrate is made using standard techniques, and then the aldehyde is reacted with an amino group on the surface.

In an alternative embodiment, a sulfhydryl linker may be used. There are a number of sulfhydryl reactive linkers known in the art such as N-Succinimidyl-3-(2-PyridylDithio)-Propionate ("SPDP"), maleimides, .alpha.-haloacetyls, and pyridyl disulfides which can be used to attach cysteine containing proteinaceous agents to the resonator surface.

Alternatively, an amino group on the bioactive target receptor may be used for attachment to an amino group on the resonator surface. For example, a large number of stable bifunctional groups are well known in the art, including homobifunctional and heterobifunctional linkers.

In an additional embodiment, carboxyl groups (either from the surface of the resonator or from the target receptor) may be derivatized using well-known linkers. For example, carbodiimides activate carboxyl groups for attack by good nucleophiles such as amines Proteinaceous target receptors may also be attached using other techniques known in the art, for example for the attachment of antibodies to polymers. It should be understood that the target receptors may be attached in a variety of ways, including those listed above. What is important is that manner of attachment does not significantly alter the ability of the target receptor to hybridize with the target entity.

§4.5 Conclusions

A major virtue of micro-fluidics systems is that they handle very small volumes (<50 μL). In this respect, a syringe needle is a micro-fluidic device for which a great deal of ancillary gear (i.e. Luer locks, valves, etc.) has been developed, and for which unique access to fluids is available either by septum or skin penetration. For a typical 22 gauge hypodermic needle the inner diameter (ID) is approx. 400 μm. Consequently, drawing 1 cm of liquid into the structure corresponds to about 1 μL. Since microspheres 30-50 μm in diameter are small in comparison to the needle inner diameter (ID) there is adequate room for several sensors. The ability to address each is because they respond in the frequency domain, allowing the fiber to be multiplexed. The key advantage of such sensors is extremely large sensitivity to both refractive index and adsorbate binding. The latter can be bound specifically leading to biological identification. With just two microspheres it is possible to compensate for common mode effects (temperature, average refractive index) or to sense two analytes. Placing an integrated sensor platform within the syringe needle provides an advantageous device for testing small amounts of body fluids, such as blood for example.

What is claimed is:

1. A sensor for determining the presence or concentration of a target substance in a body fluid, the sensor comprising:
   a) a syringe including
      1) a needle,
      2) a barrel fluidly coupled with the needle, and
      3) a plunger adapted to fit within and be slideable within the barrel; and
   b) an assembly provided within the needle of the syringe and including
      1) an optical carrier having a reflective distal end, and
      2) at least one resonator coupled with the optical carrier and provided with receptors adapted to selectively capture the target substance.

2. The sensor of claim 1 wherein the needle has an inner diameter of 150-400 μm.

3. The sensor of claim 1 wherein the optical carrier is an optical fiber, and wherein each of the at least one resonator is coupled with the optical fiber at a tapered portion.

4. The sensor of claim 3 wherein the tapered portion of the optical fiber is 1.5-4.5 μm.

5. The sensor of claim 4 wherein each of the at least one resonator has a diameter of 30-50 μm.

6. The sensor of claim 1 wherein each of the at least one resonator is a microsphere having a diameter of 30-50 μm.

7. The sensor of claim 1 wherein the optical carrier is an optical fiber, and wherein the reflective distal end of the optical fiber has a surface substantially orthogonal to an optical axis of the optical fiber.

8. The sensor of claim 1 wherein the optical carrier is an optical fiber, and wherein the reflective distal end of the optical fiber is coated with silver.

9. The sensor of claim 1 wherein the optical carrier is an optical fiber, and wherein the reflective distal end of the optical fiber has a surface which is (1) substantially orthogonal to an optical axis of the optical fiber and (2) coated with silver.

10. A method for determining the presence or concentration of a target substance in body fluid, the method comprising:

a) using a syringe, drawing a sample of the body fluid into at least a needle of the syringe, such that the sample of body fluid is brought into contact with an assembly provided within the needle of the syringe, the assembly including an optical carrier having a reflective distal end, and at least one resonator coupled with the optical carrier and provided with receptors adapted to selectively capture the target substance;
b) applying a light source to the optical carrier;
c) detecting light reflected from the optical carrier; and
d) determining the presence or concentration of the target substance in the body fluid using a property of the detected light.

11. The method of claim 10 wherein the property of the detected light is based on a shift in resonance of the resonator.

12. The method of claim 10 wherein the needle of the syringe has an inner diameter of 150-400 µm.

13. The method of claim 10 wherein the optical carrier is an optical fiber, and wherein the reflective distal end of the optical fiber has a surface substantially orthogonal to an optical axis of the optical fiber.

14. The method of claim 10 wherein the optical carrier is an optical fiber, and wherein the reflective distal end of the optical fiber is coated with silver.

15. The method of claim 10 wherein the optical carrier is an optical fiber, and wherein the reflective distal end of the optical fiber has a surface which is (1) substantially orthogonal to an optical axis of the optical fiber and (2) coated with silver.

16. A system comprising:
a) a light source;
b) a light detector;
c) means for determining a presence or concentration of a target substance using a characteristic of light detected by the light detector; and
d) a syringe-based sensor including
  1) a needle, and
  2) an assembly including both an optical carrier having a reflective distal end and at least one resonator coupled with the optical carrier and provided with receptors adapted to selectively capture the target substance, the assembly being provided within the needle and the optical carrier being optically coupled with both the light source and the light detector.

17. The system of claim 16 wherein the needle of the syringe has an inner diameter of 150-400 µm.

18. The system of claim 16 wherein the optical carrier is an optical fiber, and wherein the reflective distal end of the optical fiber has a surface substantially orthogonal to an optical axis of the optical fiber.

19. The system of claim 16 wherein the optical carrier is an optical fiber, and wherein the reflective distal end of the optical fiber is coated with silver.

20. The system of claim 16 wherein the optical carrier is an optical fiber, and wherein the reflective distal end of the optical fiber has a surface which is (1) substantially orthogonal to an optical axis of the optical fiber and (2) coated with silver.

* * * * *